(12) United States Patent
Han

(10) Patent No.: US 11,506,661 B2
(45) Date of Patent: Nov. 22, 2022

(54) DETECTION OF SERUM ANTI-FADA ANTIBODIES AND RELATED DIAGNOSTIC METHODS

(71) Applicant: Yiping Han, Bronx, NY (US)

(72) Inventor: Yiping Han, Bronx, NY (US)

(73) Assignee: The Trustees of Columbia University In the City of New York, New York, NY (US)

( * ) Notice: Subject to any disclaimer, the term of this patent is extended or adjusted under 35 U.S.C. 154(b) by 36 days.

(21) Appl. No.: 15/970,391

(22) Filed: May 3, 2018

(65) Prior Publication Data

US 2018/0246096 A1    Aug. 30, 2018

Related U.S. Application Data

(63) Continuation-in-part of application No. PCT/US2016/060595, filed on Nov. 4, 2016.

(60) Provisional application No. 62/250,660, filed on Nov. 4, 2015.

(51) Int. Cl.
  *G01N 33/569*  (2006.01)
  *C07K 16/12*   (2006.01)
  *G01N 33/574*  (2006.01)

(52) U.S. Cl.
  CPC ....... *G01N 33/56916* (2013.01); *C07K 16/12* (2013.01); *G01N 33/57419* (2013.01); *G01N 33/57484* (2013.01); *G01N 2469/20* (2013.01); *G01N 2800/065* (2013.01); *G01N 2800/60* (2013.01)

(58) Field of Classification Search
  CPC .... C07K 16/12; C12Q 1/689; G01N 2469/20; G01N 2800/065; G01N 2800/368; G01N 2800/60; G01N 33/56911; G01N 33/56916; G01N 33/57419; G01N 33/57484
  See application file for complete search history.

(56) References Cited

U.S. PATENT DOCUMENTS

| 9,670,548 | B2  | 6/2017  | Han                        |
|-----------|-----|---------|----------------------------|
| 2013/0130404 | A1* | 5/2013 | Mehra ............. G01N 33/54306 436/501 |
| 2013/0196311 | A1  | 8/2013  | Sambursky et al.           |
| 2013/0259899 | A1  | 10/2013 | Allen-Vercoe et al.        |
| 2014/0206011 | A1  | 7/2014  | Han et al.                 |
| 2014/0294882 | A1  | 10/2014 | Narayanan et al.           |

FOREIGN PATENT DOCUMENTS

| CN | 101270381       | 4/2011 |
| WO | WO 2012/045150  | 4/2012 |

OTHER PUBLICATIONS

Shin et al. PLOS One 8: e53703, pp. 1-10, 2013.*
Greenspan et al. Nature Biotechnology 17:936-937, 1999.*
Aagaard K, Riehle K, Ma J, Segata N, Mistretta TA, Coarfa C et al. A metagenomic approach to characterization of the vaginal microbiome signature in pregnancy. PLoS One Jun. 13, 2012; 7: e36466.
Cahill RJ, Tan S, Dougan G, O'Gaora P, Pickard D, Kennea N et al. Universal DNA primers amplify bacterial DNA from human fetal membranes and link Fusobacterium nucleatum with prolonged preterm membrane rupture. Mol Hum Reprod Oct. 27, 2005.
Han YW, Shi W, Huang GT, Kinder Haake S, Park NH, Kuramitsu H et al. Interactions between periodontal bacteria and human oral epithelial cells: Fusobacterium nucleatum adheres to and invades epithelial cells. Infect Immun Jun. 2000; 68: 3140-3146.
Han YW, Ikegami A, Rajanna C, Kawsar HI, Zhou Y, Li M et al. Identification and characterization of a novel adhesin unique to oral fusobacteria. J Bacteriol Aug. 2005; 187: 5330-5340.
Han YW, Shen T, Chung P, Buhimschi IA, Buhimschi CS. Uncultivated bacteria as etiologic agents of intra-amniotic inflammation leading to preterm birth. J Clin Microbiol Jan. 2009; 47: 38-47.
Han YW, Fardini Y, Chen C, Iacampo KG, Peraino VA, Shamonki JM et al. Term stillbirth caused by oral Fusobacterium nucleatum. Obstet Gynecol Feb. 2010; 115: 442-445.
Han YW, Wang X. Mobile Microbiome: Oral Bacteria in Extra-oral Infections and Inflammation. J Dent Res Jun. 2013.
Han YW. Fusobacterium nucleatum: a commensal-turned pathogen. Current opinion in microbiology Jan. 8, 2015; 23C: 141-147.
Ikegami A, Chung P, Han YW. Complementation of the fadA mutation in Fusobacterium nucleatum demonstrates that the surface-exposed adhesin promotes cellular invasion and placental colonization. Infect Immun Jul. 2009; 77: 3075-3079.
Kostic AD, Chun E, Robertson L, Glickman JN, Gallini CA, Michaud M et al. Fusobacterium nucleatum potentiates intestinal tumorigenesis and modulates the tumor-Immune microenvironment. Cell Host Microbe Aug. 14, 2013; 14: 207-215.
Liu H, Redline RW, Han YW. Fusobacterium nucleatum induces fetal death in mice via stimulation of TLR4-mediated placental inflammatory response. J Immunol Aug. 15, 2007; 179: 2501-2508.
Rubinstein MR, Wang X, Liu W, Hao Y, Cai G, Han YW. Fusobacterium nucleatum promotes colorectal carcinogenesis by modulating E-cadherin/β-catenin signaling via its FadA adhesin. Cell Host Microbe Aug. 14, 2013; 14: 195-206.
Segata N, Haake SK, Mannon P, Lemon KP, Waldron L, Gevers D et al. Composition of the adult digestive tract bacterial microbiome based on seven mouth surfaces, tonsils, throat and stool samples. Genome biology Jun. 14, 2012; 13: R42.
Wang X, Buhimschi CS, Temoin S, Bhandari V, Han YW, Buhimschi IA. Comparative microbial analysis of paired amniotic fluid and cord blood from pregnancies complicated by preterm birth and early-onset neonatal sepsis. PLoS One Feb. 2013; 8: e56131.
Xu M, Yamada M, Li M, Liu H, Chen SG, Han YW. FadA from Fusobacterium nucleatum utilizes both secreted and nonsecreted forms for functional oligomerization for attachment and invasion of host cells. J Biol Chem Aug. 24, 2007; 282: 25000-25009.

(Continued)

*Primary Examiner* — Sarvamangala Devi
(74) *Attorney, Agent, or Firm* — Knobbe, Martens, Olson & Bear, LLP

(57) ABSTRACT

The present invention relates to detecting serum anti-FadA antibodies in test samples from a patient. Additionally, aspects of the present invention provide the basis for detection of serum anti-FadA antibody levels from test samples and correlation with various conditions of clinical relevance.

6 Claims, 9 Drawing Sheets

(56) References Cited

OTHER PUBLICATIONS

Castellarin, Mauro et al. "*Fusobacterium nucleatum* Infection Is Prevalent in Human Colorectal Carcinoma." *Genome Research* 22.2 (2012): 299-306. *PMC.* Web. May 1, 2018.

Kapoor, Anoop et al. "Systemic Antibiotic Therapy in Periodontics." *Dental Research Journal* 9.5 (2012): 505-515. Print.

Kostic, Aleksandar D., et al. "Fusobacterium nucleatum potentiates intestinal tumorigenesis and modulates the tumor-immune microenvironment." *Cell host & microbe* 14.2 (2013): 207-215.

Kotby, Alyaa Amal, Nevin Mamdouh Habeeb, and Sahar Ezz El Elarab. "Antistreptolysin O Titer in Health and Disease: Levels and Significance." *Pediatric Reports* 4.1 (2012): e8. *PMC.* Web. May 1, 2018.

Liu, Hongqi, Raymond W. Redline, and Yiping W. Han. "Fusobacterium nucleatum induces fetal death in mice via stimulation of TLR4-mediated placental inflammatory response." The Journal of Immunology 179.4 (2007): 2501-2508.

Nishitani, Kohei et al. "A Diagnostic Serum Antibody Test for Patients With *Staphylococcus aureus* Osteomyelitis." *Clinical Orthopaedics and Related Research* 473.9 (2015): 2735-2749. *PMC.* Web. May 1, 2018.

Rubinstein, Mara Roxana et al. "*Fusobacterium nucleatum* Promotes Colorectal Carcinogenesis by Modulating E-Cadherin/β-Catenin Signaling via Its FadA Adhesin." *Cell host & microbe* 14.2 (2013): 195-206. *PMC.* Web. May 1, 2018.

Xu, Minghua, et al. "FadA from Fusobacterium nucleatum utilizes both secreted and nonsecreted forms for functional oligomerization for attachment and invasion of host cells." Journal of Biological Chemistry 282.34 (2007): 25000-25009.

\* cited by examiner

DETECTION OF SERUM ANTI-FADA ANTIBODIES AND RELATED DIAGNOSTIC METHODS

CROSS-REFERENCE TO RELATED APPLICATIONS

The present application is a continuation-in-part of International patent application Serial No. PCT/US2016/060595, filed Nov. 4, 2016, which claims priority to U.S. patent application Ser. No. 62/250,660, filed Nov. 4, 2015, which is hereby incorporated by reference in its entirety.

STATEMENT OF GOVERNMENT SUPPORT

This invention was made with government support under DE023332, DE014924, and CA192111 awarded by the National Institutes of Health. The government has certain rights in this invention.

FIELD OF THE INVENTION

The present invention relates to detecting serum anti-FadA antibodies in test samples. Additionally, aspects of the present invention provide the basis for detection of serum anti-FadA antibody levels from test samples and correlation with various conditions of clinical relevance.

BACKGROUND OF THE INVENTION

*Fusobacterium nucleatum* (Fn) is a long filamentous Gram-negative anaerobe, ubiquitous in the oral cavity. It is highly prevalent in biofilms associated with various oral infections including gingivitis, periodontitis, and endodontic infections (Han Y W, 2015). As an opportunistic pathogen, it is present in periodontally healthy as well as diseased sites, with the quantities in the diseased sites exceeding those in the healthy sites (Moore W E, Moore L V. 2000).

Outside the oral cavity, Fn is absent or infrequently detected under normal conditions (Aagaard K, et al. 2012; Segata N. et al., 2012). Under disease conditions, however, Fn is one of the most prevalent species involved in organ abscesses, atherosclerosis, pregnancy complications, rheumatoid arthritis, respiratory tract infections, and GI disorders (e.g. colorectal cancer (CRC), inflammatory bowel disease, and appendicitis) (Han Y W and Wang X. 2013; Han Y W, 2015).

Discovery of Fn in multiple human diseases is in part due to the advancement of microbial detection technologies, which allow an increasing number of previously overlooked microorganisms to be identified.

Previous results demonstrated that Fn specifically stimulates colorectal tumorigenesis via its unique adhesin FadA (for *Fusobacterium* adhesin A). Initial findings relating to detecting the DNA and mRNA encoding FadA and correlations with CRC were described in US Patent Application No. 20140206011.

However, there remains a need for quick and reliable diagnostics for infection or colonization with Fn and for correlations useful in assessing risk for conditions relating to adverse pregnancy outcomes, as well as colorectal (CRC) and related cancers.

Embodiments of the present invention provide the basis for detection of serum anti-FadA antibodies and correlation with various conditions of clinical relevance.

SUMMARY OF THE INVENTION

In certain embodiments, the present invention relates to a method of detecting colonization of a patient with *Fusobacterium nucleatum* (Fn) comprising: a) obtaining a sample from a patient; and b) contacting the patient sample with a binding agent capable of binding an anti-*Fusobacterium* adhesin A (FadA) antibody, and c) detecting binding between the anti-FadA patient antibody and said binding agent.

In certain embodiments, the present invention relates to a method of detecting serum anti-*Fusobacterium* adhesin A (FadA) antibody in a patient sample comprising a) obtaining a sample from a patient; and b) contacting the patient sample with a binding agent capable of binding an anti-FadA antibody, and c) detecting binding between the anti-FadA patient antibody and said binding agent.

In certain embodiments, the present invention relates to a method for detecting adverse pregnancy status in a patient comprising: a) contacting a patient sample with a binding agent capable of binding an anti-*Fusobacterium* adhesin A (FadA) antibody, b) detecting binding between the anti-FadA patient antibody and said binding agent; and c) determining a test level of serum antibodies to FadA in the sample obtained or derived from the patient, and based upon a comparison of the test level of the serum FadA antibodies to a reference, identifying the patient as at risk for one or more adverse pregnancy events selected from the group consisting of chorioamnionitis, preterm birth, stillbirth, neonatal sepsis, and preeclampsia, when the test level of serum antibodies to FadA is above the reference level.

In certain embodiments, the present invention relates to a method of detecting a pre-cancerous colorectal stage of a patient comprising: a) contacting a patient sample with a binding agent capable of binding an anti-*Fusobacterium* adhesin A (FadA) antibody, b) detecting binding between the anti-FadA patient antibody and said binding agent; and further determining whether the detected level of anti-FadA patient antibody is elevated above a baseline or reference level, wherein an elevated above baseline level of anti-FadA patient antibody indicates that the patient is at a pre-cancerous colorectal cancer stage.

In certain embodiments, the patient is a mammal.

In certain embodiments, the patient is identified as not colonized with *Fusobacterium nucleatum* by detecting a baseline value or absence of anti-FadA patient antibody.

In certain embodiments, the method further comprises determining that the animal has an early, intermediate or chronic *Fusobacterium nucleatum* (Fn) infection based on detecting that the patient level of serum antibodies to FadA is above a baseline level.

In certain embodiments, the binding agent capable of binding an anti-*Fusobacterium* adhesin A (FadA) patient antibody comprises a detectable label.

In certain embodiments, detecting the presence of the antibodies is determined using a lateral flow device.

In certain embodiments, detecting the presence of the antibodies is determined using a fluorescent bead-based multiplex assay.

In certain embodiments, the method further comprises administering an effective amount of an antibiotic selected from the group consisting of penicillin, piperacillin, cefoxitin, clindamycin, metronidazole and imipenem, and combinations thereof, upon detection of patient FadA serum antibodies at a level above baseline.

In certain embodiments, the method further comprises detecting DNA and/or mRNA encoding FadA or FadA protein levels in the patient sample.

In certain embodiments, the colonization of said patient with *Fusobacterium nucleatum* (Fn) indicates an infectious condition.

In certain embodiments, the infectious condition is periodontitis or appendicitis.

In certain embodiments, the patient sample is selected from the group consisting of a colon biopsy, saliva, rectal swab, or a bodily fluid.

In certain embodiments, the bodily fluid is selected from the group consisting of wherein the bodily fluid comprises at least one of blood, amniotic fluid, lung aspirate, saliva, or synovial fluid.

In certain embodiments, the binding agent capable of binding an anti-*Fusobacterium* adhesin A (FadA) patient antibody comprises a recombinant FadA protein.

The present invention also relates to a method of detecting colonization of a patient with *Fusobacterium nucleatum* (Fn) comprising: a) contacting a patient sample with a binding agent capable of binding an anti-*Fusobacterium* adhesin A (FadA) patient antibody, and b) detecting the presence or absence of said anti-FadA patient antibody in said sample based on binding, or lack thereof, of said binding agent to said anti-FadA patient antibody, thereby detecting colonization of said patient with *Fusobacterium nucleatum* (Fn).

In additional embodiments, the invention relates to a method for diagnosing adverse pregnancy status in a patient comprising, a) contacting a patient sample with a binding agent capable of binding an anti-*Fusobacterium* adhesin A (FadA) patient antibody, and b) determining a test level of serum antibodies to FadA in the sample obtained or derived from the patient, and based upon a comparison of the test level of the serum FadA antibodies to a reference, identifying the patient as at risk for one or more adverse pregnancy events selected from the group consisting of chorioamnionitis, preterm birth, stillbirth, neonatal sepsis, and preeclampsia, if the test level of serum antibodies to FadA is above the reference level.

In additional embodiments, the invention relates to a method of detecting a pre-cancerous colorectal stage of a patient comprising: a) contacting a patient sample with a binding agent capable of binding an anti-*Fusobacterium* adhesin A (FadA) patient antibody, and b) detecting the presence or absence of said anti-FadA patient antibody in said sample based on binding, or lack thereof, of said binding agent to said anti-FadA patient antibody, further determining whether the detected level of anti-FadA patient antibody is elevated above a baseline or reference level, wherein an elevated above baseline level of anti-FadA patient antibody indicates that the patient is at a pre-cancerous colorectal cancer stage.

In certain embodiments, the patient is a mammal. In certain embodiments, the patient is identified as not colonized with *Fusobacterium nucleatum* by determining an absence of the anti-FadA patient antibody.

In certain embodiments, the method further comprises determining that the animal has an early, intermediate or chronic *Fusobacterium nucleatum* (Fn) infection based on the determining the presence or the absence of the antibodies, and further determining whether the test level of serum antibodies to FadA is above a reference level.

In certain embodiments, determining the presence or the absence of the antibodies is determined using a lateral flow device. In additional embodiments, determining the presence or the absence of the antibodies is determined using a fluorescent bead-based multiplex assay.

In certain embodiments, the colonization of said patient with *Fusobacterium nucleatum* (Fn) indicates periodontitis.

In certain embodiments, the anti-FadA patient antibody detected is anti-FadA IgA.

In certain embodiments, the elevated anti-FadA IgA patient antibody level indicates that the patient is at risk for developing colorectal cancer, pre-colorectal polyps, adenomas, or a related condition.

DETAILED DESCRIPTION OF THE INVENTION

Figure 1:
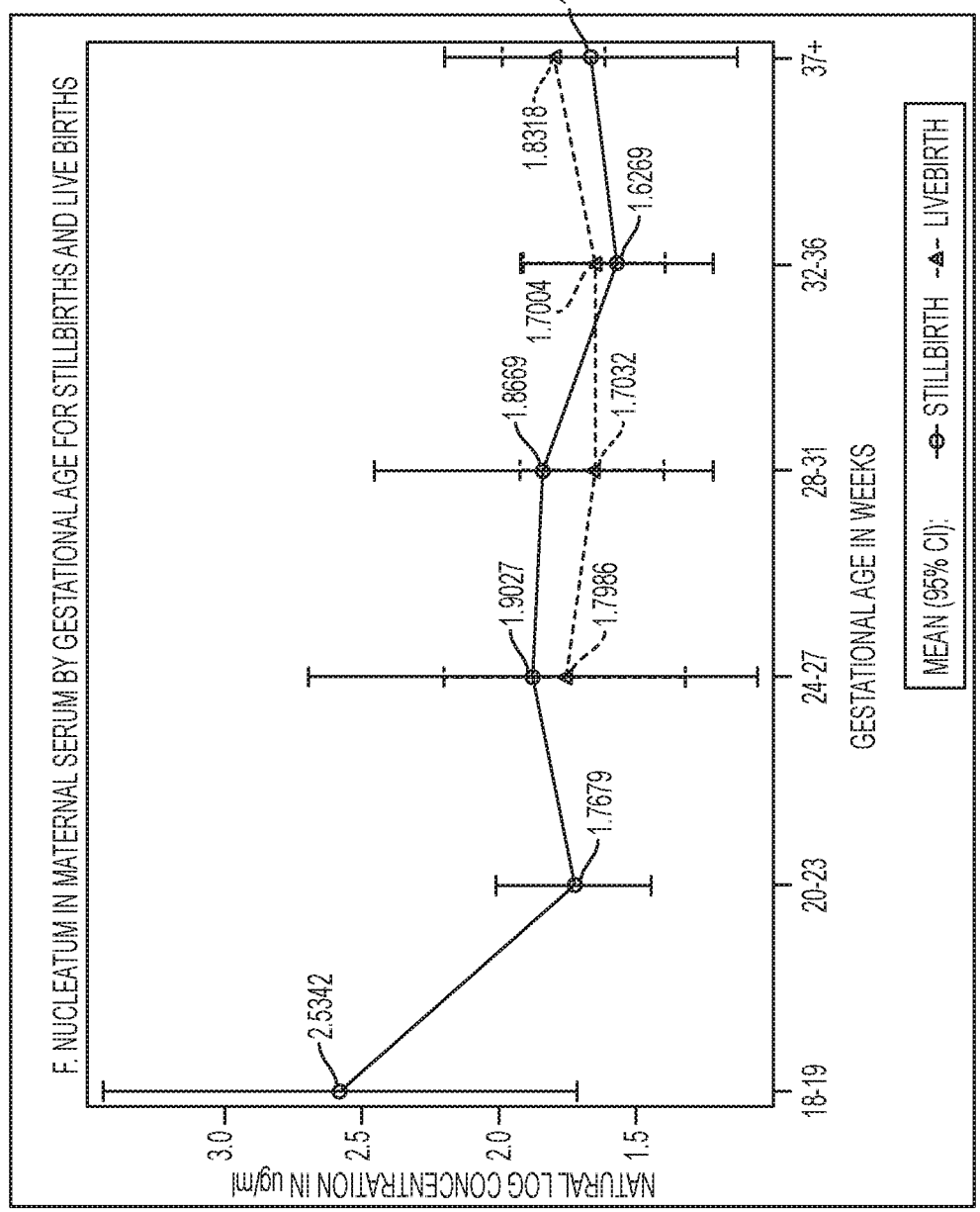
FIG. 1 shows graphic comparisons of maternal serum antibody titers against FadA as determined by ELISA. Samples were grouped by gestational age at delivery as following: 18-19 weeks (wks), 20-23 wks, 24-27 wks, 32-36 wks, and >37 wks (term). Solid line: stillbirths; dashed line: live births (including preterm and term). Vertical bars indicate 95% confidence intervals.

The present invention relates to detecting serum anti-FadA antibodies in test samples, e.g. patient samples. Additionally, aspects of the present invention provide the basis for detection of serum anti-FadA antibody levels from test samples and correlation with various conditions of clinical relevance.

FadA is a Key Virulence Factor of Fn.

Fn is an "adhesive" organism, binding to a wide variety of host cells, including epithelial and endothelial cells, fibroblasts, and immune cells. The FadA adhesin plays an important role in mediating Fn binding and invasion of various host cells.

FadA is a small peptide with two different forms: a non-secreted intact form (pre-FadA, 15.5 kDa) consisting of 129 amino-acid (aa) residues (the sequence can be found at GenBank: AAY47043), and a secreted mature form (mFadA, 13.6 kDa) consisting of 111 aa (as described in US Patent Application No. 20140206011). Pre-FadA and mFadA are both required for function, forming the active FadAc complex (Xu M., et al. 2007). When expressed in *E. coli*, FadA enhances bacterial attachment and invasion of epithelial and endothelial cells.

The present invention provides a method for detecting serum anti-FadA antibodies in a sample from a pregnant patient/subject. In certain embodiments, the present invention provides for correlating the risk of a negative outcome such as stillbirth with the level of anti-FadA antibodies determined from a sample from a pregnant patient (See FIGS. 1 and 3). The method comprises obtaining, providing or collecting a tissue or fluid sample (such as a blood or serum sample) from said subject, and then determining the presence or absence of anti-FadA antibodies in said sample, or increased levels of anti-FadA antibodies in said sample as compared to a normal or control subject. The presence of anti-FadA antibodies in said sample, or increased levels of anti-FadA antibodies in said sample, indicates said subject is afflicted with or at least at risk of developing one or more adverse pregnancy outcomes such as: chorioamnionitis, preterm birth, stillbirth, neonatal sepsis, eclampsia, or preeclampsia. Pregnancy stages and complications which are impacted by Fn colonization of the mother include: chorioamnionitis, preterm birth, stillbirth, neonatal sepsis, fetal and neonatal lung development, eclampsia and preeclampsia.

The present invention further provides a method for detecting or screening for the presence or likelihood of developing colorectal cancer or pre-colorectal polyps or adenomas or related conditions, in a subject. The method comprises obtaining, providing or collecting a tissue or fluid sample (such as a blood or serum sample) from said subject, and then determining the presence or absence of anti-FadA antibodies in said sample, or increased levels of anti-FadA antibodies in said sample as compared to a normal or control subject. The presence of anti-FadA antibodies in said sample, or increased levels of anti-FadA antibodies in said sample, indicates said subject is afflicted with or at least at risk of developing colorectal cancer or pre-colorectal polyps, or adenomas or a related condition.

The present invention further provides a method of detecting colonization of a patient with *Fusobacterium nucleatum* (Fn). The method comprises: a) contacting a patient sample with a binding agent capable of binding an anti-*Fusobacterium* adhesin A (FadA) patient antibody, and b) detecting the presence or absence of said anti-FadA patient antibody in said sample based on binding, or lack thereof, of said binding agent to said anti-FadA patient antibody, thereby detecting colonization of said patient with *Fusobacterium nucleatum* (Fn).

The present invention further provides a method for detecting or screening for the presence or likelihood of an infectious condition in a subject. The method comprises obtaining, providing or collecting a tissue or fluid sample (such as a blood or serum sample) from said subject, and then determining the presence or absence of anti-FadA antibodies in said sample, or increased levels of anti-FadA antibodies in said sample as compared to a normal or control subject. The presence of anti-FadA antibodies in said sample, or increased level of anti-FadA antibodies in said sample, indicates said subject is afflicted with or at least at risk of developing an infectious condition such as appendicitis, other organ abscesses, neonatal lung development complications, GI disorders (e.g., colorectal carcinogenesis and inflammatory bowel disease), combinations of these conditions, or a related condition.

In certain embodiments, detection methods as described herein can be utilized in combination with methods for detecting the DNA and/or mRNA encoding FadA or FadA protein levels (such as those described in US Patent Application No. 20140206011). Such combination of methods, detecting anti-FadA antibody and also detecting the DNA or mRNA encoding FadA will lead to a definitive diagnosis in certain instances and will serve to rule out a potential false positive result.

Under normal, healthy conditions, the level of anti-FadA antibody detectable in a patient sample is an extremely low, nearly undetectable baseline amount. Thus, in certain embodiments, a baseline reference for anti-FadA antibody is between 0-1.5 µg/ml (natural log concentration) for a normal, individual without any infectious conditions. In alternative embodiments, a baseline reference for anti-FadA antibody is between 0-about 40 µg/ml (natural log concentration) for a normal, individual without any infectious conditions.

In certain embodiments, the present invention encompasses a kit comprising a container, said container comprising at least one binding agent for detecting anti-FadA antibodies, and a detection agent.

The test, patient, or biological sample assayed in the method can be any biological sample that would be expected to contain antibodies. The biological sample is preferably a biological liquid. In various embodiments, the biological sample comprises blood or serum. The biological sample can be obtained from the mammal using any suitable technique and can be used directly in determining the presence or absence of the antibodies. Alternatively, the sample can be derived from the biological sample by subjecting it to a processing step, such as a processing step performed to isolate or purify blood, serum, CSF, or components of any such biological liquids.

In non-limiting examples, the antibodies to FadA (also referred to herein as anti-FadA antibodies) can be detected using any number of immunodetection techniques, which include but are not necessarily limited to Western blot, enzyme-linked immunosorbent assay (ELISA), a snap test, multiplex antibody detection techniques of various kinds, or any modification of such assays that are suitable for detecting antibodies of interest. Many suitable antibody detection methods are described including, for example, in U.S. Pat. No. 9,034,656. The patient antibody to FadA can be an IgG or IgA, or other forms.

In particularly preferred embodiments, the patient antibody to FadA is IgA and is detected in patient serum or plasma.

In yet additional embodiments, the invention relates to the use of any of the antibody or antibody fragments described herein for diagnostic use.

In yet additional embodiments, the invention relates to a kit comprising any of the antibodies or antigen binding fragments described herein.

In yet additional embodiments, the invention relates to a complex comprising the FadA polypeptide and any one of the antibody or antigen binding fragments described herein.

Detection Kits

The present invention also provides kits comprising the components of the combinations of the invention in kit form. A kit of the present invention includes one or more components including, but not limited to, an antibody or antigen binding fragment, as discussed herein, which specifically binds human FadA antibody, and optionally a second antibody or antigen binding fragment that binds human FadA protein.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an antibody capable of binding human anti-FadA antibody and optionally, human peptide FadA or an antigenic fragment thereof, packaged in a container, such as a vial or bottle, and further comprising a label attached to or packaged with the container, the label describing the contents of the container and providing indications and/or instructions regarding use of the contents of the container to treat one or more disease states as described herein.

The detection kits disclosed herein may also be prepared that comprise at least one of the antibody, peptide, antigen-binding fragment, disclosed herein and instructions for using the composition as a detection reagent. Containers for use in such kits may typically comprise at least one vial, test tube, flask, bottle, syringe or other suitable container, into which one or more of the detection and/or therapeutic composition(s) may be placed, and preferably suitably aliquoted. Where a second detection agent is also provided, the kit may also contain a second distinct container into which this second detection composition may be placed. Alternatively, a plurality of compounds may be prepared in a single composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorogenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In related embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

Definitions

Terms have the meanings ascribed to them in the text unless expressly stated to the contrary. It must be noted that, as used herein, the singular forms "a", "an," and "the" include plural references unless the context clearly dictates otherwise. In addition, the following terms have the following meanings.

"Patient" or "subject" refers to mammals and includes human and veterinary subjects.

Antigen and Immunogen

An "antigen" (from antibody-generating) or "immunogen" is a substance that prompts the generation of antibodies and can cause an immune response. They may also be used for diagnostic or patient selection or characterization purposes. An "immunodominant antigen" is defined as an antigen for which a higher relative number of T cells will be specific during an immune response, compared to the numbers of T cells with T cell receptors that recognize other antigens.

Antibody

Antibodies (also known as immunoglobulins (Ig)) are gamma globulin proteins that are found in blood or other bodily fluids of vertebrates, and are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies are produced by B cells. There are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter.

Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The unique part of the antigen recognized by an antibody is termed an "epitope." These epitopes bind with their antibody in a highly specific interaction, called induced fit, which allows antibodies to identify and bind only their unique antigen in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection. Production of antibodies is the main function of the humoral immune system.

Enzyme-Linked Immunoabsorbent Assay (ELISA)

Enzyme-Linked ImmunoSorbent Assay, also called ELISA, Enzyme ImmunoAssay or EIA, is a biochemical technique used to detect the presence of an antibody or an antigen in a sample. In ELISA, an unknown amount of antigen is affixed to a surface, and then a specific antibody is washed over the surface so that it can bind to the antigen. This antibody is linked to an enzyme, and in the final step a substance is added that the enzyme can convert to some detectable signal. Thus in the case of fluorescence ELISA, when light of the appropriate wavelength is shone upon the sample, any antigen/antibody complexes will fluoresce so that the amount of antigen in the sample can be inferred through the magnitude of the fluorescence. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized the detection antibody is added, forming a complex with the antigen. The detection antibody can be covalently linked to an enzyme, or can itself be detected by a secondary antibody which is linked to an enzyme through bioconjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates enabling much higher sensitivity.

The term "effective amount" of a compound is a quantity sufficient to achieve a desired therapeutic and/or prophylactic effect, for example, an amount which results in the alleviation, prevention of, or a decrease in the symptoms associated with a disease that is being treated, "Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Inhibitors" and "antagonists," or "activators" and "agonists," refer to inhibitory or activating molecules, respectively, e.g., for the activation of, e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a compound that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., samples not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-

128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least ten times the control.

"Small molecule" is defined as a molecule with a molecular weight that is less than 10 kDa, typically less than 2 kDa, preferably less than 1 kDa, and most preferably less than about 500 Da. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins, have been described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra).

Standard techniques for characterizing ligand/receptor interactions are available (see, e.g., Coligan, et al. (2001) *Current Protocols in Immunology*, Vol. 4, John Wiley, Inc., New York).

Examples

High Levels of Anti-FadA Antibodies Correlate with Multiple Adverse Outcomes and Diseases
Adverse Pregnancy Outcomes Fn is one of the most prevalent species in intrauterine infection associated with chorioamnionitis, preterm birth, stillbirth, and neonatal sepsis (Cahill R J, et al. 2005; Han Y. W., Shen T., et al., 2009; Han Y W, Fardini Y., et al. 2010; Kostic A. D., et al. 2013; Rubinstein M. R. et al., 2013; Wang X. et al., 2013). Using a well-established pregnant mouse model, we have demonstrated that Fn colonize specifically in the mouse placenta through hematogenous transmission, causing TLR4-mediated inflammatory responses, leading to preterm and term fetal death (Han Y W, Redline R W, et al. 2004; Liu H, Redline R W, Han Y W 2007). The fadA-deletion mutant is defective in colonizing the mouse placenta (Ikegami A, Chung P, Han Y W 2009).
Comparison of Maternal Serum Antibody Titers Against FadA by ELISA Samples were grouped by gestational age at delivery as follows: 18-19 weeks (wks), 20-23 wks, 24-27 wks, 32-36 wks, and >37 wks (term). Solid line: stillbirths; dashed line, live births (including preterm and term). Vertical bars indicate 95% confidence intervals. These data illustrate high anti-FadA antibody titers among stillbirths at an early gestational stage, i.e., between 18-19 wks. These anti-FadA antibody levels are significantly higher than for stillbirths ($p<0.03$) at other gestational stages (FIG. 1). Thus, these data indicate that testing pregnant patients for anti-FadA antibody titers could improve outcomes by identifying those at risk for still birth and providing appropriate antibiotic or inhibitory peptide treatment at that stage. It would be expected that reducing anti-FadA antibody titers at least during the early stages of gestation, to correspond to a level at or below a reference or baseline level (e.g. not greater than about 1.8 µg/ml, as indicated in FIG. 1), would improve outcomes by reducing the risk of pregnancy complications including one or more of the following: chorioamnionitis, preterm birth, stillbirth, neonatal sepsis, and preeclampsia.

Additionally, it is expected that monitoring newborns for fetal lung development will be useful in instances when levels of anti-FadA antibody titers in the mother were tested to be above a reference or baseline level during pregnancy. Thus, testing or monitoring such newborns for a period of from several weeks, to several months for anti-FadA antibody titers will inform whether any antibiotic treatment for Fn colonization of the newborn will be needed.
Colorectal Carcinogenesis Fn has been shown to stimulate colorectal cancer growth in vitro, and in xenograft and Apcm$^{min/+}$ mice (Kostic A. D. et al. 2013; Rubinstein M. R., et al. 2013). FadA plays a key role in stimulating tumorigenic responses. We have detected elevated anti-FadA antibody levels in patients with precancerous polyps, i.e. adenoma; as well as in patients with colorectal cancer, i.e. carcinoma, as shown in FIG. 2.

Figure 2:
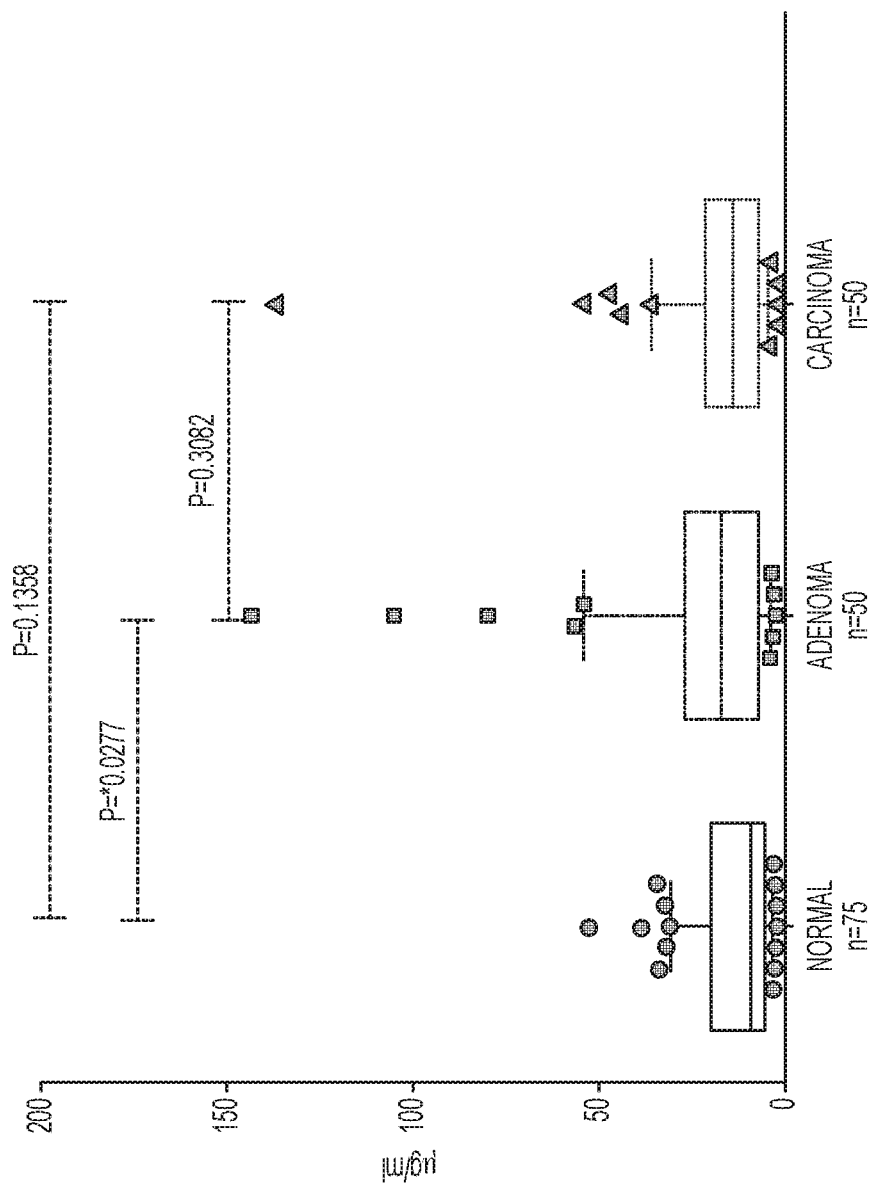
FIG. 2 shows graphic comparisons of serum antibody titers against FadA by ELISA between normal individuals (n=75), patients with precancerous polyps (adenoma, n=50), and patients with colorectal cancer (carcinoma, n=50). The boxes represent the $25^{th}$ and $75^{th}$ percentiles and the lines within the boxes indicate the median values. The whiskers indicate the $10^{th}$ and $90^{th}$ percentiles. The data were analyzed by one-way ANOVA followed by Mann-Whitney non-parametric test. * $p<0.05$.

FIG. 2 shows a comparison of serum antibody titers against FadA by ELISA between normal individuals (n=75), patients with precancerous polyps (adenoma, n=50), and patients with colorectal cancer (carcinoma, n=50). The boxes represent the $25^{th}$ and $75^{th}$ percentiles and the lines within the boxes indicate the median values. The whiskers indicate the 10$^{th}$ and 90$^{th}$ percentiles. The data were analyzed by one-way ANOVA followed by Mann-Whitney non-parametric test. * p<0.05. Thus, it would be expected that assaying for anti-FadA antibody in patient serum and detecting a level of anti-FadA antibody above baseline or reference (as indicated by the normal values of <about 50 µg/ml at the left of the graph in FIG. 2) would be predictive of precancerous polyps and would also be an indicator of likelihood of progression to CRC. Thus, it would be expected that reducing anti-FadA titers (by for example reducing or eliminating the Fn with antibiotics or inhibitory peptides) in such patients would lead to improved outcomes, and at least for those with precancerous polyps, could lead to prevention of the cancerous stage.

Figure 3:
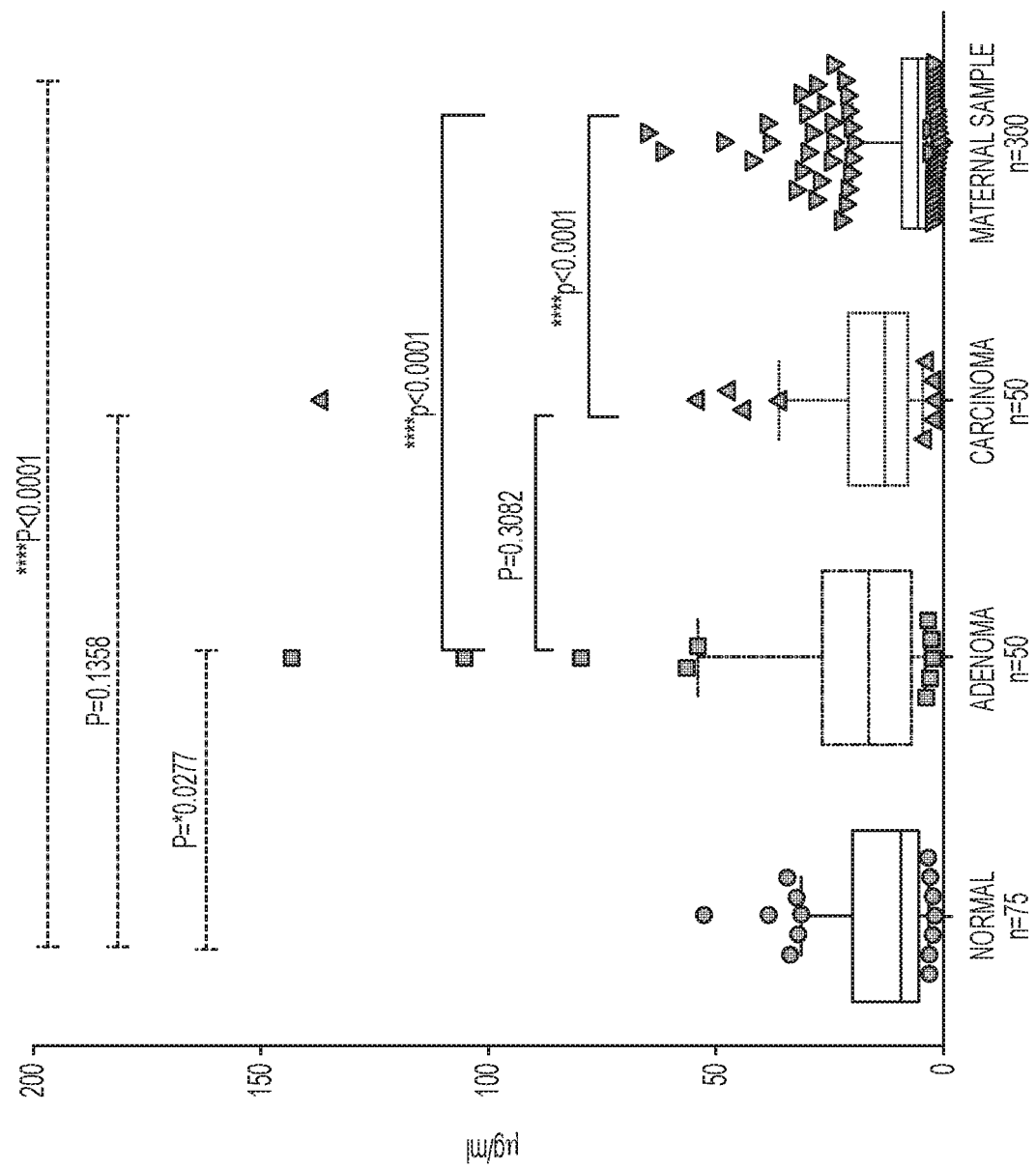
FIG. 3 shows graphic comparisons of serum antibody titers against FadA by ELISA between normal individuals (n=75), patients with precancerous polyps (adenoma, n=50), patients with colorectal cancer (carcinoma, n=50), and pregnant women (including stillbirths, and preterm and term live births; n=300). The boxes represent the $25^{th}$ and $75^{th}$ percentiles and the lines within the boxes indicate the median values. The whiskers indicate the $10^{th}$ and $90^{th}$ percentiles. * $p<0.05$; **** $p<0.0001$.

FIG. 3 is a combination graphic showing a comparison of serum antibody titers against FadA by ELISA between normal individuals (n=75), patients with precancerous polyps (adenoma, n=50), patients with colorectal cancer (carcinoma, n=50), and pregnant women (including stillbirths, and preterm and term live births; n=300). The boxes represent the 25$^{th}$ and 75$^{th}$ percentiles and the lines within the boxes indicate the median values. The whiskers indicate the 10$^{th}$ and 90$^{th}$ percentiles. * p<0.05; **** p<0.0001.

Periodontal Disease

Figure 4:
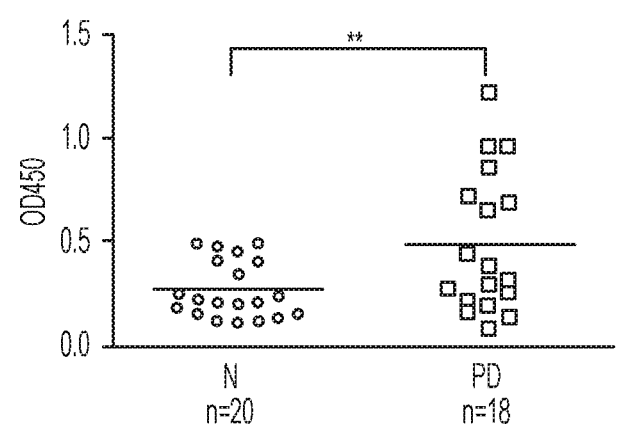
FIG. 4 shows results from ELISA assays of serum FadA antibody titers of periodontally healthy individuals (N; n=20) and patients with periodontitis (PD, n=18). Horizontal bars represent the means. ** $p<0.01$.

FIG. 4 shows results from an ELISA assay to measure serum antibody titers against FadA in healthy controls versus patients with periodontitis. Patients with periodontitis exhibited elevated serum anti-FadA antibody titers compared to the periodontally healthy controls (FIG. 4), suggesting a potential role of anti-FadA antibody in periodontitis. Thus, these data indicate that testing patients for anti-FadA titers could improve outcomes by identifying those at risk for periodontitis and providing appropriate antibiotic or inhibitory peptide treatment at an early stage. It would be expected that reducing anti-FadA titers at least during the early stages of periodontitis or pre-periodontitis, to correspond to a level at or below a reference or baseline level (e.g. not greater than about 0.5 as measured at OD450, as indicated in FIG. 4), would improve outcomes and could lead to prevention of the periodontitis stage.

Infectious Condition—Appendicitis

An ELISA assay to measure serum antibody titers against FadA in healthy controls versus patients with appendicitis will be conducted. Patients with appendicitis are expected to exhibit elevated serum anti-FadA antibody titers compared to healthy controls, suggesting a potential role of anti-FadA antibody, or colonization of an individual with Fn in appendicitis. Thus, these data indicate that testing patients for anti-FadA titers could improve outcomes by identifying those at risk for appendicitis and providing appropriate antibiotic or inhibitory peptide treatment at an early stage. It would be expected that reducing anti-FadA titers at least during the early stages of appendicitis or pre-appendicitis, to correspond to a level at or below a reference or baseline level, would improve outcomes and could lead to prevention of the acute appendicitis and potentially avoid surgery to remove the infected appendix.

In view of these results, it is expected that detection of elevated serum anti-FadA antibody titers will be useful for detecting adverse pregnancy outcomes, organ abscesses, and GI disorders (e.g., colorectal carcinogenesis as shown herein, and also inflammatory bowel disease), and appendicitis. Additionally, once serum FadA antibodies above baseline are detected in a patient's serum, a course of antibiotic treatment and/or other therapies aimed at reducing or eliminating Fn colonization can be selected/determined. Such treatment would typically include one or more of the following antibiotics: penicillin, piperacillin, cefoxitin, clindamycin, metronidazole and imipenem.

Anti-FadA Antibody Detection Methods

The ELISA plates are coated with purified recombinant FadA protein. Following washing, blocking and washing again, the test or control samples (e.g., body fluids and their dilutions) are added to the plates. After incubation, the plates are washed again, followed by addition of horse radish peroxidase-conjugated secondary antibodies. After incubation, washing and color development according to standard protocols is carried out, the quantity of anti-FadA antibodies were determined according to standard curves. The following reagents were utilized:

Sigma A2290-1 ml Goat anti-human IgG (γ-chain specific) Lot #1001873334 dilution 1:2000;
Goat anti-human IgA secondary antibody HRP (Thermo scientific, Catalog #PA1-74395) dilution 1:6000;
Goat anti-mouse IgG(H+L) Poly-HRP secondary Antibody HRP conjugate (Thermo scientific, Catalog #32230) dilution 1:10000;
Substrate: TMB substrate (1-Step™ ultra TMB-ELISA substrate solution, Thermo scientific, catalog #34028).

Evaluation of Data and Summary of FIGS. 5-9

It has been determined that a number of factors affect the control group results when analyzing anti-FadA titers, including sex, age, and other factors. Thus, the data in FIGS. 5-9 (some of it the re-analysis of earlier data with smaller/more defined control groups) illustrate different trends and some surprising results from those observed in the initial data evaluated in FIGS. 1-4.

For FIGS. 5-9 the controls were matched for race and age. In the Case Western Reserve samples, they were additionally matched for gender. In the Cornell samples, they were additionally matched for smoking.

Figure 5:
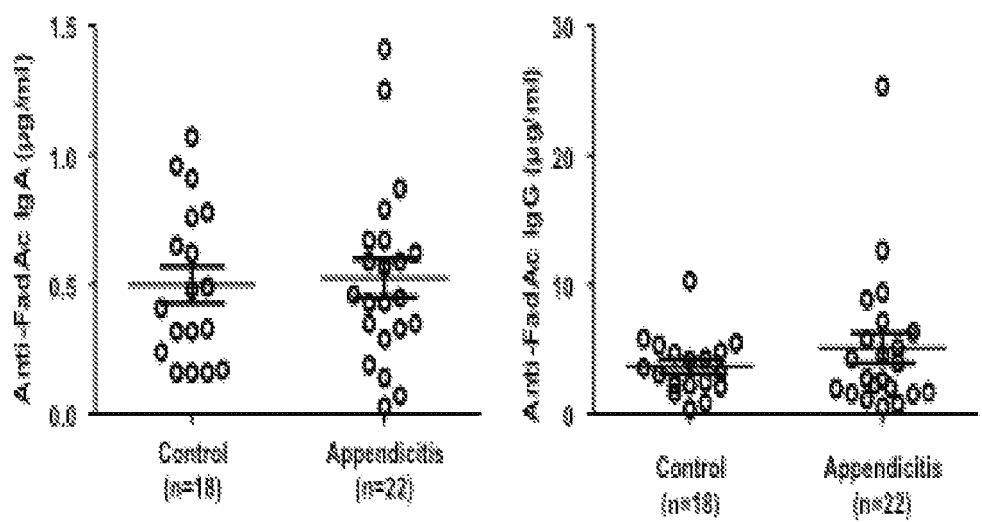
FIG. 5 shows graphs illustrating that there is no difference between the control and the appendicitis groups in anti-FadA titers (whether detecting anti-FadA IgA or anti-FadA IgA.

In FIG. 5, the analysis illustrates that there is no difference between the control and the appendicitis groups in anti-FadA titers (whether detecting anti-FadA IgA or anti-FadA IgA.

Figure 6:
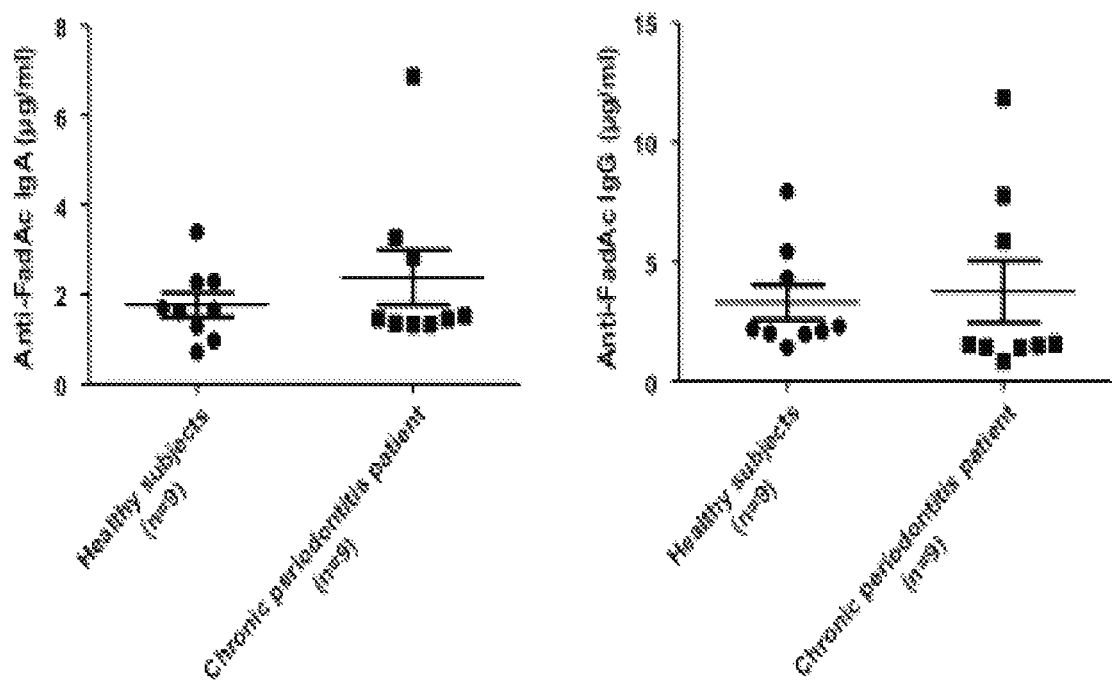
FIG. 6 shows graphs illustrating that there is no difference between the control and periodontitis groups in anti-FadA titers.

Similarly, FIG. 6 shows that there is no difference between the control and periodontitis groups in anti-FadA titers.

Figure 7:
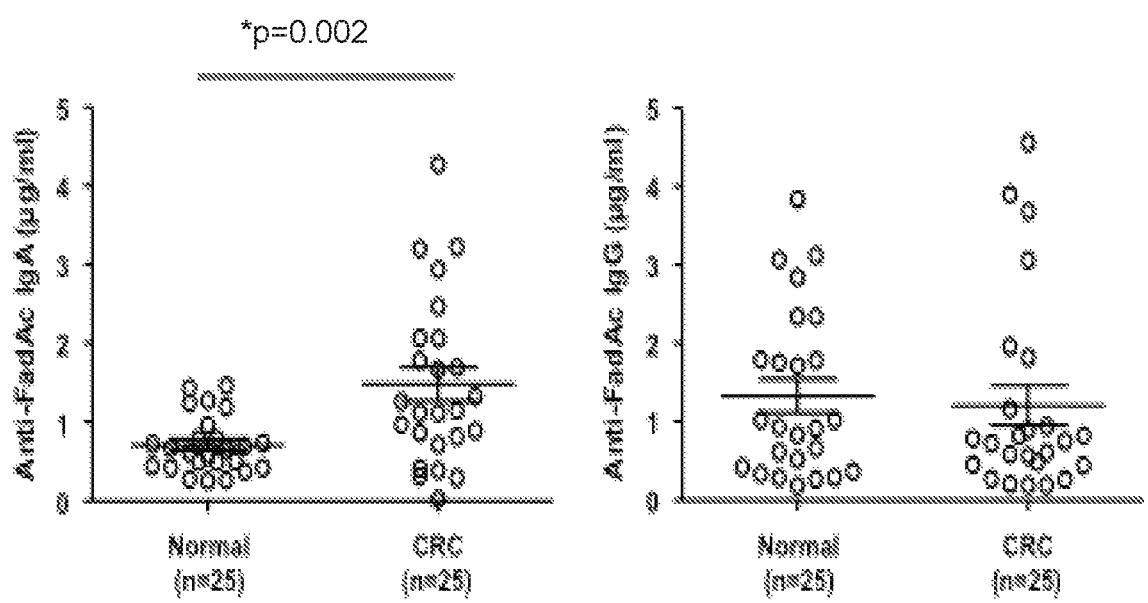
FIG. 7 shows results using samples provided from Case Western Reserve University. These data illustrate a surprising significant difference between the normal and colon cancer group (CRC) in anti-FadA IgA antibody titers (p=0.002), but not in IgG titers.

FIG. 7 shows results using samples provided from Case Western Reserve University. Evaluating these samples, showed a surprising significant difference between the normal and colon cancer group (CRC) in anti-FadA IgA antibody titers (p=0.002), but not in IgG titers.

Figure 8:
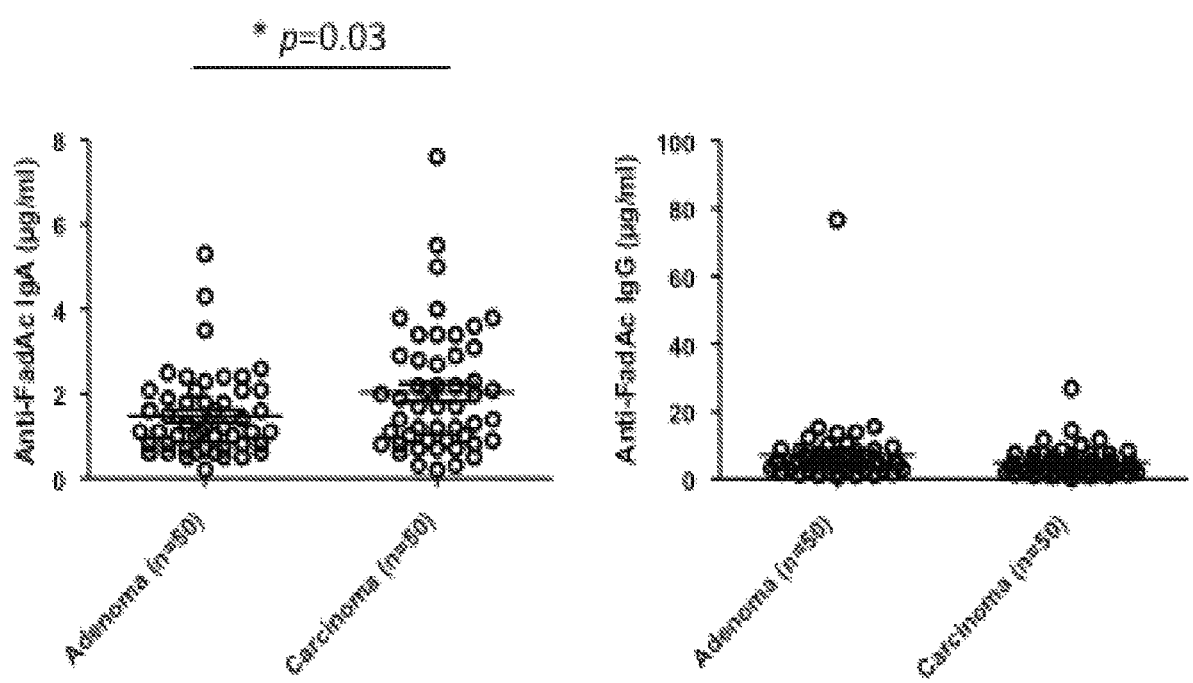
FIG. 8 shows results using samples provided from Weill Cornel Medical School. Evaluation of these samples also showed a surprising significant difference between the advanced adenoma group (>2 cm) and CRC group in anti-FadA IgA antibody titers (p=0.03), but not in IgG titers.

FIG. 8 shows results using samples provided from Weill Cornel Medical School. Evaluation of these samples also showed a surprising significant difference between the advanced adenoma group (>2 cm) and CRC group in anti-FadA IgA antibody titers (p=0.03), but not in IgG titers.

Figure 9:
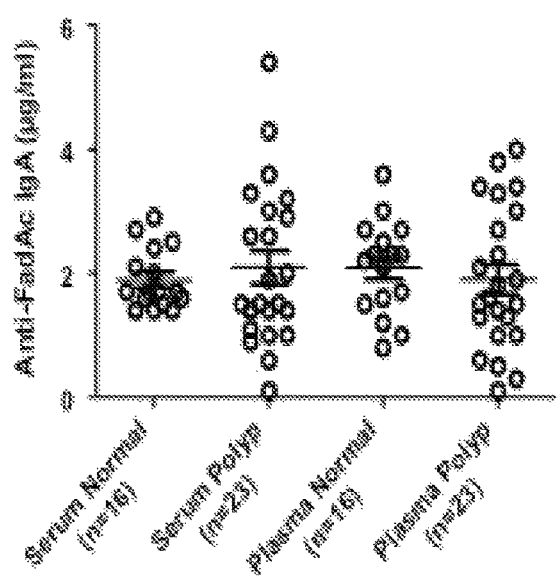
FIG. 9 shows results using samples provided from the Division of Liver and Digestive Diseases at Columbia University. These data illustrate no detection difference whether serum or plasma samples were used to measure anti-FadA antibody titers.
Figure 9:
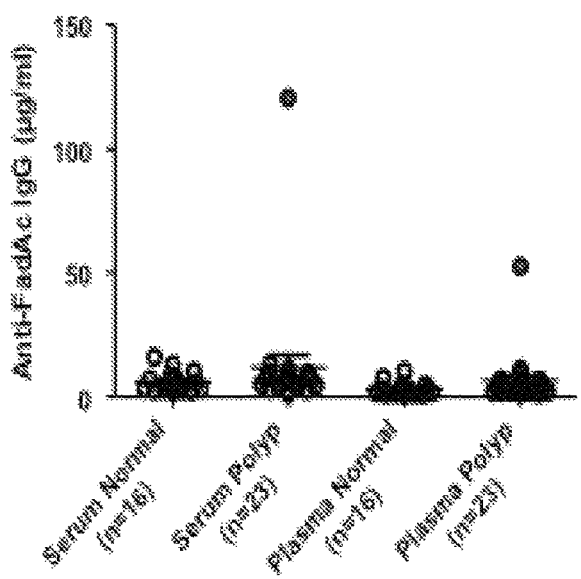

Finally, FIG. 9 shows results using samples provided from the Division of Liver and Digestive Diseases at Columbia University. These results illustrate no detection difference whether or not serum or plasma samples were used to measure anti-FadA antibody titers.

Materials and Methods

Purification of FadA

The recombinant FadA protein was prepared from *E. coli* BL21 (DE3) carrying pYWH471-6 as previously described {Xu, 2007 #24}. Briefly *E. coli* BL21 (DE3) carrying pYWH471-6 was grown in 6 flasks each containing 400 ml Luria-Bertani (LB) media supplemented with 100 µg/ml of ampicillin to mid-log phase, followed by induction with 1 mM Isopropyl ß-D-1-thiogalactopyranoside (IPTG; Sigma-Aldrich, St. Louis, Mo.) for 2.5 hr at 37° C. The bacteria were harvested by centrifugation at 8000 g for 5 min, the pellet (approximately 12 g) was incubated with 100 ml of buffer A (50 mM $NaH_2PO_4$, 300 mM NaCl, 8 M Urea, pH 8.0) at 4° C. overnight. After removing cell debris and insoluble material by centrifugation at 6000 g for 10 min, the clear lysate was split into two halves and each half was incubated with 5 ml TALON® Metal Affinity Resins (Clontech Laboratories, Inc., Mountain View, Calif.) for 4 hr at 4° C. Each mixture was then transferred to a glass chromatography column (3×15 cm) and unbound materials were washed with 150 ml of buffer A. The bound materials were eluted with 30 ml of Buffer B (50 mM $NaH_2PO_4$, 300 mM NaCl, 8M Urea, pH 5.0) and the elute was serially collected in 3 ml aliquots. The fractions containing recombinant FadA were pooled and dialyzed in against PBS pH 7.2 in dialysis membranes with MWCO of 6-8 kDa (Spectra/Por® 1; Spectrum Laboratories, Inc., Ranch Dominguez, Calif.). The quantity of purified recombinant FadA was determined using BCA protein assay kit (ThermoFisher Scientific, Waltham, Mass.).

Enzyme-Linked Immunosorbent Assay (ELISA)

The levels of anti-FadA IgA and IgG were determined by indirect ELISA. Briefly, ninety-six-well ELISA plates (Thermo Scientific™ Immuno Clear Standard Modules; ThermoFisher Scientific) were coated with 100 µl of purified recombinant FadA (2 µg/ml) in 0.2 M carbonate/bicarbonate buffer (pH 9.4) at 4° C. overnight. After washing the plates with wash buffer (100 mM $NaH_2PO_4$, 150 mM NaCl, 0.05% TWEEN 20, pH 7.2) five times in a microplate washer (SI-4000; Scientific Industries Inc., Bohemia, N.Y.), each well was blocked with 100 µl of blocking buffer (100 mM $NaH_2PO_4$, 150 mM NaCl, 0.05% TWEEN 20, 2% BSA, pH 7.2) at room temperature for 2 hr. Following 3 washes with wash buffer, an aliquot of 100 µl of serially diluted blood samples (diluted from 1:250 to 1:2000), or anti-FadA monoclonal antibody 5G11 3G8 diluted to 0.4, 0.7, 1.4, 2.9, 5.8, and 23 ng/ml in blocking buffer, or just the blocking buffer alone, were added to the wells and incubated at room temperature for 1 hr. After washing the plates for five times, each well was incubated with 100 µl of goat anti-human IgA-HRP (1:6000 dilution; PA1-74395, ThermoFisher Scientific), or goat-anti-human IgG-HRP (1:1,000-10,000 dilution; A2290, Sigma-Aldrich), or goat anti-mouse IgG-HRP (1:10,000-12,000 dilution; 62-6520, ThermoFisher Scientific) at room temperature for 1 hr. The plates were washed six times followed by incubation with 100 µl substrate solution (1-Step Ultra TMB-ELISA; ThermoFisher Scientific) at room temperature for 30 min. The reaction was terminated by adding 100 µl 2 M $H_2SO_4$ and the absorbance at 405 nm was measured using an automated microplate reader (Synergy HT; BioTek, Winooski, Vt.). The background values were provided in wells with secondary antibodies alone, which were subtracted from all measurements. The standard curve was generated using the monoclonal antibody 5G11 3G8. The quantity of anti-FadA IgA and IgG was determined based on the standard curve. All measurements were performed in duplicate.

REFERENCES

Aagaard K, Riehle K, Ma J, Segata N, Mistretta T A, Coarfa C et al. A metagenomic approach to characterization of the vaginal microbiome signature in pregnancy. PLoS One 2012; 7: e36466.

Cahill R J, Tan S, Dougan G, O'Gaora P, Pickard D, Kennea N et al. Universal DNA primers amplify bacterial DNA from human fetal membranes and link *Fusobacterium nucleatum* with prolonged preterm membrane rupture. Mol Hum Reprod 2005.

Han Y W, Shi W, Huang G T, Kinder Haake S, Park N H, Kuramitsu H et al. Interactions between periodontal bacteria and human oral epithelial cells: *Fusobacterium nucleatum* adheres to and invades epithelial cells. Infect Immun 2000; 68: 3140-3146.

Han Y W, Redline R W, Li M, Yin L, Hill G B, McCormick T S. *Fusobacterium nucleatum* induces premature and term stillbirths in pregnant mice: implication of oral bacteria in preterm birth. Infect Immun 2004; 72: 2272-2279.

Han Y W, Ikegami A, Rajanna C, Kawsar H I, Zhou Y, Li M et al. Identification and characterization of a novel adhesin unique to oral fusobacteria. J Bacteriol 2005; 187: 5330-5340.

Han Y W, Shen T, Chung P, Buhimschi I A, Buhimschi C S. Uncultivated bacteria as etiologic agents of intra-amniotic inflammation leading to preterm birth. J Clin Microbiol 2009; 47: 38-47.

Han Y W, Fardini Y, Chen C, Iacampo K G, Peraino V A, Shamonki J M et al. Term stillbirth caused by oral *Fusobacterium nucleatum*. Obstet Gynecol 2010; 115: 442-445.

Han Y W. *Fusobacterium nucleatum* interaction with host cells. In: Kolenbrander P (ed). *Oral microbial communities: genomic inquiry and interspecies communication*. ASM press, 2011.

Han Y W, Wang X. Mobile Microbiome: Oral Bacteria in Extra-oral Infections and Inflammation. J Dent Res 2013.

Han Y W. Commentary: Oral bacteria as drivers for colorectal cancer. J Periodontol 2014; 85: 1155-1157.

Han Y W. *Fusobacterium nucleatum*: a commensal-turned pathogen. Current opinion in microbiology 2015; 23C: 141-147.

Ikegami A, Chung P, Han Y W. Complementation of the fadA mutation in *Fusobacterium nucleatum* demonstrates that the surface-exposed adhesin promotes cellular invasion and placental colonization. Infect Immun 2009; 77: 3075-3079.

Kostic A D, Chun E, Robertson L, Glickman J N, Gallini C A, Michaud M et al. *Fusobacterium nucleatum* potentiates intestinal tumorigenesis and modulates the tumor-Immune microenvironment. Cell Host Microbe 2013; 14: 207-215.

Liu H, Redline R W, Han Y W. *Fusobacterium nucleatum* induces fetal death in mice via stimulation of TLR4-mediated placental inflammatory response. J Immunol 2007; 179: 2501-2508.

Moore W E, Moore L V. The bacteria of periodontal diseases. Periodontol 2000 1994; 5: 66-77.

Rubinstein M R, Wang X, Liu W, Hao Y, Cai G, Han Y W. *Fusobacterium nucleatum* promotes colorectal carcinogenesis by modulating E-cadherin/β-catenin signaling via its FadA adhesin. Cell Host Microbe 2013; 14: 195-206.

Segata N, Haake S K, Mannon P, Lemon K P, Waldron L, Gevers D et al. Composition of the adult digestive tract bacterial microbiome based on seven mouth surfaces, tonsils, throat and stool samples. Genome biology 2012; 13: R42.

Wang X, Buhimschi C S, Temoin S, Bhandari V, Han Y W, Buhimschi I A. Comparative microbial analysis of paired amniotic fluid and cord blood from pregnancies complicated by preterm birth and early-onset neonatal sepsis. PLoS One 2013; 8: e56131.

Xu M, Yamada M, Li M, Liu H, Chen S G, Han Y W. FadA from *Fusobacterium nucleatum* utilizes both secreted and nonsecreted forms for functional oligomerization for attachment and invasion of host cells. J Biol Chem 2007; 282: 25000-25009.

INCORPORATION BY REFERENCE

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

Unless defined otherwise, all technical and scientific terms used herein have the same meaning as commonly understood by one of ordinary skill in the art to which this invention belongs. In the case of conflict, the present specification will control. All percentages and ratios used herein, unless otherwise indicated, are by weight.

What is claimed is:

1. A method of reducing colonization of *Fusobacterium nucleatum* (Fn) in a mammalian patient comprising:
   (a) obtaining a serum or plasma sample from the patient;
   (b) contacting the patient sample with a purified *Fusobacterium*-adhesin A (FadA) peptide capable of specifically binding to an anti-FadA antibody, wherein the FadA peptide is an active FadA complex (FadAc) of Fn expressed recombinantly in *E. coli*, wherein the FadAc comprises intact pre-FadA peptide of 15.5 kDa and mature FadA (mFadA) peptide of 13.6 kDa;
   (c) detecting the specific binding between the FadA peptide and the anti-FadA antibody;
   (d) determining a level of the anti-FadA antibody in the patient sample;
   (e) identifying the patient as being colonized with the Fn when the level of the anti-FadA antibody is above a baseline level of antibody specific to the FadA peptide observed in corresponding normal healthy mammalian subjects; and
   (f) providing antibiotic treatment to the patient against Fn colonization when the level of the anti-FadA antibody determined in step (d) is greater than the baseline anti-FadA antibody level, thereby reducing the anti-FadA antibody level in the patient to below the baseline anti-FadA antibody level and reducing the Fn colonization in the patient.

2. The method of claim 1, wherein the FadA peptide is attached to a detectable label.

3. The method of claim 1, wherein the level of the anti-FadA antibody is determined using a lateral flow device or a fluorescent bead-based multiplex assay.

4. The method of claim 1, wherein the of the anti-FadA antibody is an IgG or IgA.

5. The method of claim 1, wherein the baseline level of the antibody to the FadA peptide is less than 1.8 micrograms per ml and wherein the reducing of the anti-FadA antibody level by the antibiotic treatment to less than the baseline level reduces the risk of pregnancy complications in the patient.

6. The method of claim 1, wherein the baseline level of the antibody to the FadA peptide is less than 50 micrograms per ml and wherein the reducing of the anti-FadA antibody level by the antibiotic treatment to less than the baseline level reduces the risk of colorectal cancer in the patient.

* * * * *